United States Patent [19]
Gorlich et al.

[11] Patent Number: 5,183,834
[45] Date of Patent: Feb. 2, 1993

[54] PASTY DENTAL VENEER MAKING COMPOSITION

[75] Inventors: Karl J. Gorlich, Fuerth/Odw.; Fritz U. Bauer, Liederbach; Joerg Konetzka, Darmstadt, all of Fed. Rep. of Germany

[73] Assignee: Dentsply G.m.b.H., Dreleich, Fed. Rep. of Germany

[21] Appl. No.: 333,474

[22] Filed: Apr. 5, 1989

[51] Int. Cl.$^5$ ................................. A61K 6/08
[52] U.S. Cl. .................... 523/105; 523/115; 523/116; 523/117; 524/299; 524/430; 433/228.1
[58] Field of Search ............... 523/105, 113, 115, 116, 523/117; 524/299, 430; 433/228.1

[56] References Cited

U.S. PATENT DOCUMENTS

| | | | |
|---|---|---|---|
| 3,825,518 | 7/1974 | Sheerness et al. | 260/42.52 |
| 4,038,257 | 7/1977 | Suzuki et al. | 260/75 NK |
| 4,328,325 | 5/1982 | Marquardt et al. | 525/451 |
| 4,330,283 | 5/1982 | Michl et al. | 433/201 |
| 4,424,333 | 1/1984 | O'Conner | 528/75 |
| 4,483,759 | 11/1984 | Szycher et al. | 204/159.24 |
| 4,650,550 | 3/1987 | Milnes et al. | 204/38.7 |
| 4,873,269 | 10/1989 | Nakazato | 523/115 |
| 5,009,597 | 4/1991 | Schaefer | 523/115 |

FOREIGN PATENT DOCUMENTS

| | | |
|---|---|---|
| 0011734 | 6/1980 | European Pat. Off. |
| 0011735 | 6/1980 | European Pat. Off. |
| 0026398 | 4/1981 | European Pat. Off. |
| 0033750 | 11/1983 | European Pat. Off. |
| 2069517 | 8/1981 | United Kingdom |

*Primary Examiner*—Paul R. Michl
*Assistant Examiner*—Tae H. Yoon
*Attorney, Agent, or Firm*—Dale R. Lovercheck; Edward J. Hanson, Jr.

[57] ABSTRACT

A heat cured pasty composition adapted to form a dental veneer which is resistant or immune to interdental cracks while in use on crowns and bridges. The composition includes polymerizable urethane-acrylic monomer, inorganic fillers, pyrogenic silica, heat activated polymerization initiators, and fractured organic filler particles. Heat polymerization of the composition above about 100° C. forms a polymer which has a microhardness of at least HV 0.1/10 18.0 Kp/mm$^2$, and an impact strength of at least 2.0 KJ/m$^2$.

6 Claims, No Drawings

PASTY DENTAL VENEER MAKING COMPOSITION

BACKGROUND

The present invention relates to an improved veneer paste used primarily in dentistry.

Self-cured polymeric veneer material has gained broad acceptance for use in preparing and repairing dental appliances, such as crowns and bridges, as is described by Milnes et al in U.S. Pat. No. 4,650,550. Such materials have good abrasion resistance, color stability, impact strength, bending strength and microhardness suitable for their use as a replacement for dentition similar to that described in U.S. Pat. No. 3,825,518 to Foster and in European Patents EP 26398, EP 11734 and EP 11735 to Bayer; and EP 33750 to IVOCLAR.

It has been found, however, that prior art heat cured pasty veneer materials are subject to interdental cracks, and surprisingly, it has been found that such interdental cracks can be substantially reduced or eliminated by the use of a veneer composition that is cured at relatively high temperatures, and contains a milled organic filler having particle sizes in a particular range. It is believed that the irregular (fractured, split or crushed) shape and size distribution of the milled organic fillers used in the composition provide the observed improved properties.

It is an object of the present invention to provide an improved heat cured pasty veneer material that is resistant to interdental cracks.

SUMMARY OF THE INVENTION

A pasty dental veneer material is provided. The material is adapted for polymerization above about 100° C. and comprises by weight about 10-90% polymerizable monomers (binders), about 0-80% inorganic fillers (coarse), about 5-60% pyrogenic silica (microfine), about 0.2-10% polymerization initiators, and about 0-70% milled polymerized organic fillers.

The composition of the invention is characterized in that when it is cured, it has good water storage color stability when tested for 3 weeks at 60° C., a shelf life of at least 2 years at 22° C., an impact strength of at least 2.0 KJ/m$^2$, bending strength of at least 60 N/mm$^2$, a microhardness of at least HV 0.1/10 18.0 Kp/mm$^2$ and an abrasion resistance showing less than 5.0 mg weight loss in a standard test.

In a preferred embodiment, the organic fillers used in the composition have a mean particle size less than about 64 um and about 27-37% by weight of the organic filler has a particle size less than about 25 um.

DETAILED DESCRIPTION OF THE INVENTION

The polymerizable pasty dental veneer material of the invention is adapted for a heat cure above about 100° C., preferably about 115° C., and accordingly can be cured after its application to a dental appliance in a conventional water polymerization device. In the preferred embodiment the paste may be cured in a water polymerization device at about 115° C. for about 15 minutes or in a hot-air polymerization device (Airomat, available from Vita) at about the same temperature for a comparable period of time.

The pasty dental veneer material of the invention comprises by weight about 10-90% polymerizable monomers (binders), about 0.0-80% inorganic fillers (coarse), about 5.0-60% pyrogenic silica (microfine), about 0.2-10% initiators and about 0.0-70% milled polymerized organic fillers. In a preferred embodiment, it is desirable that the inorganic fillers and the organic fillers together comprise at least about 24% by weight of the veneer composition.

According to the invention, the organic filler particles are milled to a mean particle size less than about 64 um. The milling process produces a defined mixture of split (crushed) and spherical polymer particles. If desired, the percentage of spherical polymer particles in the filler mixture may be determined entirely by the length of time that the filler is subjected to the milling operation, and it is preferred that spherical particles comprise less than about 30%, more preferably less than 10% of the organic filler.

It has been found that pasty veneer compositions that employ only spherical organic filler particles when in use have a tendency to be subject to interdental cracks. It has also been discovered that when the filler particles used in the composition of the invention are milled, providing filler particles with irregular shapes (fractured, split or crushed), that the tendency toward the development of interdental cracks in use is substantially reduced or eliminated.

In the preferred embodiment, the best results have been obtained when 27-90%, more preferably 27-70% by weight of the milled organic filler particles are less than 25 um.

Conventional additives, such as inhibitors, fluorescing agents, pigments, plasticizers and oxidation stabilizers, and other conventional additives may be added to the compositions of the invention a desired.

In a preferred embodiment of the invention, the polymerizable monomer (binder) will be an urethane-acrylic derivative such as Plex 6661-0 available from

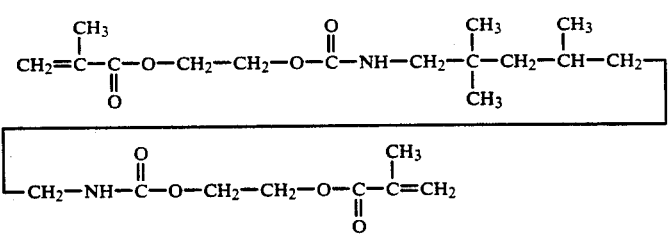

The monomer Plex 6661-0 is the reaction product of 2 moles hydroxyethyl methacrylate and 1 mole 2,2,4-trimethyl-hexamethylendiisocyanate. Di(meth)acrylate or poly functional (meth)acrylate alone and/or mixtures thereof or other similar monomers or mixtures thereof, can be used in the compositions of the invention. Exemplary of suitable monomers that can be used in the composition are 1,6-hexanedioldi(meth)acrylate, 1,12-dodecanedioldi(meth)acrylate, ethyleneglycol-di(meth)acrylate, diethyleneglycoldi(meth)acrylate, triethyleneglycoldi(meth)acrylate, tetraethylenegly-coldi(meth)acrylate, 1,3-propanedioldi(meth)acrylate, 1,4-butanedioldi(meth)acrylate, 1,10-decanedioldi-(meth)acrylate, neopentylglycoldi(meth)acrylate, etc. Di(meth)acrylate can furthermore be used as a reaction product with bisphenol A (2,2-bis(4-hydroxyphenyl)propane) and one or more molecules of ethylene oxide, propylene oxide or mixtures thereof. Reaction products of hydroxyalkyl(meth)acrylates with polyisocyanates, for example hexamethylenediisocyanate, isophorondiisocyanate etc., and reaction products of bisphenol A and glycidylalkyl(meth)acrylates (ratio 1:1, 1:2) with polyisocyanates, for example 2 glycidyl(meth)-acrylate, 1 mole bisphenol A and 1 mole hexamethylene-diisocyanate (NCO-monomer) can also be used. Tri(meth)-acrylates obtained from trimethylolpropane, glycerin, 1,2,4-butanetriol or pentaerythritol, as well as tetra-(meth)acrylates from polyols can also be used. Exemplary of such compounds is tetramethylolmethane, pentaerythritol. Additional suitable polymers will be apparent to those skilled in the art.

The preferred inorganic filler is a glass having a refractive index that closely matches the refractive index of the cured matrix of the polymer composition, such as potassium-sodium-aluminum-silicate glass. In the preferred embodiment the glass filler is silanated, preferably with gamma-methacryloyl oxypropyltrimethoxysilane. Other silanating agents, which are well known in the art, can also be used to make the surface of the glass filler hydrophobic.

Preferably, the inorganic filler used is milled (crushed) to a mean grain size of less than about 40 um, more preferably the grain size will be in the range of 1-10 um. The milling procedure produces filler grains that have a crushed form that has an irregular or rough surface area. The pyrogenic silica used in the composition has a grain size less than 100 nm, preferably a mean grain size of about 40 nm.

Those skilled in the art will recognize that other types of inorganic glass filler can be used, provided that their refractive index is similar to the refractive index of the polymer matrix in the cured product. Also, at least a portion, 5-75%, preferably 10-70% of the inorganic filler may be glass beads having a mean grain size less than about 40 um, preferably 1-10 um.

The preferred inorganic filler used in the composition is silanized potassium-sodium-aluminum silicate glass known as WH-1380 available from Dentsply GmbH, Dreieich, Germany. Those skilled in the art will recognize that precipitated silica, titanium dioxide, magnesium oxide, quartz, sodium-aluminum-silicate glass and mixtures thereof ca be used as fillers. Other suitable inorganic fillers will be apparent to those skilled in the art.

The preferred pyrogenic silica used in the composition is highly dispersed silanized pyrogenic silica (HDK) as sold by Wacker. The BET surfaces and density of pyrogenic silicas are variable. Preferred is a silica having a BET surface of approximately 170 m$^2$/g and a bulk density of 90 g/l. Another suitable silica is Aerosil (Degussa). The BET surface of the silica should be between 10 to 400 m$^2$/g, preferably between 50-300 m$^2$/g. The pyrogenic silica should be hydrophobic. Also mixtures of pyrogenic silica with different BET-surfaces may be used. Other suitable pyrogenic silicas will be apparent to those skilled in the art.

The preferred polymerization initiators of the composition are peroxide initiators such as tert-butyl perisononanoate, and non-peroxide temperature active initiators such as benzopinacol, and mixtures thereof. Exemplary of such initiators are peroxides and/or pinacol derivatives such as dibenzoyl peroxide, tert-butylperbenzoate, tert-butyl peroctoate, 2,2'-dialkyl-benzopinacol and 2,2'-dichlorobenzopinacol. Other polymerization initiators which supply radicals upon heating, for example azo derivatives, can be used. Other suitable initiators will be apparent to those skilled in the art.

2,4-dihydroxy benzophenone may be used as a preferred U.V stabilizer in the composition of the invention. Other U.V. stabilizers that may be used are well known to those skilled in the art. Exemplary of such U.V. stabilizers are hydroxybenzophenone, hydroxyphenyl-benzotriazole, cinnamates, oxalic anilides etc.

The preferred "organic" fillers, cross-linked and/or non-cross-linked polymers of the invention, comprise (meth)acrylates and/or poly functional (meth)acrylates and mixtures thereof.

The polymers of the invention may be prepared in bulk polymerization, and/or by a method of suspension polymerization. The polymers may also contain pyrogenic and/or precipitated silica, glass, ceramic, metal oxides or other customary inorganic fillers. The inorganic filler may comprise preferably 2-95%, most preferably 10-80% by weight of the total weight of the organic filler.

For example, suspension polymers made from 99% monomer plex 6661-0 and 1% trimethylolpropanetrimethacrylate can be used or a polymer made from 58.5% monomer plex 6661-0, 40% HDK H 2000 (a hydrophobic pyrogenic silica having a grain size of about 40 nm, available from Wacker GmbH, Burghausen, Germany) and 1% trimethylolpropanetrimethacrylate can be used. In the preferred embodiment, the organic filler comprises polymer AD 56 available from AD Plastics, Blackpool, U.K.

In the preferred embodiment, the pasty dental veneer composition of the invention comprises by weight about 10-90%, preferably 20-60% monomer; 0-80%, preferably 4-50% silanized glass; 5-60%, preferably 10-55% pyrogenic silica; 0.01-5%, preferably 0.05-3% peroxide initiator; 0.01-5%, preferably 0.05-3% heat activated nonperoxide initiator; 0-5%, preferably 0.05-2% U.V. stabilizer; and 0-70%, preferably 10-60% organic polymer filler.

The preferred composition of the invention comprises by weight 31-34% urethane-acrylic monomer, 7-11% silanized glass, 17-21% pyrogenic silica, 0.3-0.6% alkylacylperoxide, 0.3-0.6% heat activated nonperoxide initiator, 0.05-0.5% U.V. stabilizer and 35-39% organic polymer filler.

The compositions of the invention have been found to have the following properties:
1. Good handling properties
2. Polymerization at 115° C.
3. Good abrasion resistance. Abrasion resistance less than 5.0 mg. (as determined by the toothbrush test)
4. Good water storage color stability (tested for 3 weeks at 60° C.)
5. Shelf life at 22° C.=2 years; at 26° C.=1 year; at 50° C.=2 weeks.
6. Impact strength (DIN* 53 435)=2.0 kj/m$^2$.
7. Bending strength (DIN 53 435)=60 N/mm$^2$.
8. Microhardness (DIN 50 133) HV (Vickers Hardness) 0.1/10 18.0 Kp/mm$^2$.

9. Good polishing properties, can be finished to a high gloss.

*DIN=Deutsche Industrie Norm. The number following DIN in each case represents the specific standard test employed.

The following illustrates examples of the above tests.

Microhardness (DIN50 133) was measured in terms of kiloponds/mm² by a Durimet Kleinlasthaertegeraet (Leitz) with a load of 100 gm.

Abrasion resistance was determined as described by H. Uetz et al. in Dental-Labor 22, 596-604, 1974, in an article entitled "Abriebverhalten von Kunststoffen fuer den dentalen Anwendungsbereich".

The water storage stability test was carried out by comparing a control specimen with separate test specimens that have been stored in water for 3 weeks at 60° C. This test is used to provide some indication of the color stability that the cured material will have in use by the patient.

The shelf life test is carried out by placing an unopened package (in the form in which it is to be sold) of the material in a 50° C. oven for 3 weeks. After 3 weeks the sample is observed for possible discoloration and for its handling properties.

EXAMPLE 1

Preparation of the pasty Veneer composition. The polymeric organic filler material was prepared by crushing or fracturing spherical polymer AD-56 beads having a mean size of about 64 um in a ball mill, using porcelain balls, to a mean particle size of about 40 um. When viewed under a microscope, it could be observed that about 10% of the polymer particles remained in a spherical form, the other particles were flattened, fractured and crushed and generally were of irregular shape (the particles had the appearance of broken glass, i.e. sharp-edged and irregular particles were produced similar to what might be expected when a window is broken). About 32% of the particles were less than about 25 um.

The inorganic glass filler was made by preparing a potassium-sodium-aluminum silicate glass frit (WH-1380) and crushing the glass frit in a vibration mill to a mean grain size of about 5 um.

The pyrogenic silica (HDK H 2000) was used in the form provided directly from the manufacturer (mean grain size of 40 nm).

The pasty veneer composition of the invention was prepared in a planetary mixer. All the tools and containers used in the preparation were chromium, synthetic (e.g. teflon), and ceramic plated.

60 gm Plex 6661-0 monomer, 1 gm tert-butyl-perisononanoate, 1 gm benzopinacol, and 0.5 gm 2,4-dihydroxybenzophenone were charged into the mixer and mixed until the blend was homogeneous. Thereafter, 70 gm crushed (mean particle size about 40 um, 32% less than 25 um) polymer AD-56, 20 gm silanized crushed glass (mean grain size about 5 um) and 40 gm pyrogenic silica (mean grain size about 40 nm) were added to the mixture sequentially at a rate that provided for even mixing of the materials at all times in the mixing process. The temperature was kept at or below 20° C.

The mixture provided a composition that comprised by weight about

| | |
|---|---|
| 31.17% | Plex 6661-0 |
| 10.39% | silanized crushed glass |
| 20.78% | pyrogenic silica |

-continued

| | |
|---|---|
| 0.52% | tert-butyl-perisononanoate |
| 0.52% | benzopinacol |
| 0.26% | 2,4-dihydroxybenzophenone and |
| 36.36% | fractured particles of AD-56 polymer. |

EXAMPLE 2

This example demonstrates the importance of the particle size, and the milling (fracturing) of the filler particles, to the physical properties obtained by the veneer paste.

The table describes the particle size distribution of the organic filler material AD 56 (milled and unmilled) as used in the specific preferred composition prepared in Example 1.

Pastes of each composition were prepared and applied to metal frames and cured, at 115° C. in a water curing apparatus for 15 minutes, for testing.

| POLYMER AD-56 | Particle Size | | | |
|---|---|---|---|---|
| BATCH | 2.5-25 | 25-64 | 64-80 | >100 um |
| # J 6/87 unmilled | 39.5 | 60.0 | 0.5 | 0 |
| # B 002 milled | 26.0 | 64.0 | 10.0 | 0 |
| # B 001 milled | 32.0 | 66.0 | 2.0 | 0 |
| # E 7/G2/88 milled | 47.0 | 52.5 | 0.5 | 0 |
| # E 8/88 milled | 99.0 | 1.0 | 0 | 0 |

Physical properties and performance on metal frames of the materials made from the above mentioned polymer batches are described in the table below:

| POLYMER AD-56 BATCH | Impact Strength kJ/m² | Bending Strength N/mm² | Bending Angle degrees | Cracks |
|---|---|---|---|---|
| # J 6/87 unmilled | 2.1 | 65 | 5.9 | yes (after 1-2 hrs) |
| # B 002 milled | 2.5 | 85 | 10.2 | yes (after 24 hrs) |
| # B 001 milled | 2.8 | 93 | 11.1 | none |
| # E 7/G2/88 milled | 3.2 | 100 | 13.9 | —* |
| # E 8/88 milled | 2.1 | 54 | 7.1 | —* |

*no veneers made (see below)

As can be seen from the data in the table, veneer compositions containing milled particles in which a substantial portion, but not all, of the particles have a size below 25 um exhibit the best properties. From the data in the table it can be concluded that it is preferred to mill the suspension polymers and to achieve particle size distribution similar to that shown in the B 001 batch.

It is preferred that the composition have 30-90% fine grain content and most preferably a small grain content of 30-80%.

The B 001 batch has the best overall properties to prevent interdental cracks and to maintain superior handling. The batches with a higher content of fine grain showed poorer handling properties. Therefore no veneers were made.

While present embodiments of the invention and methods of practicing the same have been illustrated and described, it will be recognized by those skilled in the art that this invention may be otherwise variously embodied and practiced within the scope of the following claims.

What is claimed is:

1. A pasty dental composition adapted for heat polymerization above about 100° C. to form a polymer useful as a dental veneer comprising by weight about
   (a) 20-60% polymerizable urethane-acrylic binders,
   (b) 4.0-50% crushed silanized glass fillers,
   (c) 10-55% pyrogenic silica,
   (d) 0.05-3% alkylacylperoxide,
   (e) 0.05-3% heat activated nonperoxide initators,
   (f) 0.05-2% U.V. stabilizers, and
   (g) 10-60% fractured acrylic polymers.

2. A pasty dental composition adapted for heat polymerization above about 100° C. to form a polymer useful as a dental veneer comprising by weight about
   (a) 31-34% polymerizable uretane-acrylic binders,
   (b) 7-11% crushed silanized glass fillers,
   (c) 17-21% pyrogenic silica,
   (d) 0.3-0.6% tert-butyl-perisononanoate,
   (e) 0.3-0.6% benzopinacol,
   (f) 0.05-0.5% 2,4-dihydroxybenzophenone, and
   (g) 35-38% fractured acrylic polymers.

3. The pasty dental composition adapted for heat polymerization above about 100° C. of claim 1 wherein said composition is polymerized to form a veneer.

4. The pasty dental composition adapted for heat polymerization above about 100° C. of claim 2 wherein said composition is polymerized to form a veneer.

5. A pasty dental composition adapted for heat polymerization above about 100° C. to form a veneer polymer having an impact strength of at least 2.0 KJ/M$^2$, comprising by weight about
   (a) 20-60% polymerizable urethane-acrylic binders,
   (b) 4.0-50% crushed silanized glass fillers,
   (c) 10-55% pyrogenic silica,
   (d) 0.05-3% alkylacylperoxide,
   (e) 0.05-3% heat activated nonperoxide initators,
   (f) 0.05-2% U.V. stabilizers, and
   (g) 10-60% fractured acrylic polymers.

6. A pasty dental composition adapted for heat polymerization above about 100° C. to form a veneer polymer having an impact strength of at least 2.0 KJ/M$^2$, comprising by weight about
   (a) 31-34% polymerizable urethane-acrylic binders,
   (b) 7-11% crushed silanized glass fillers,
   (c) 17-21% pyrogenic silica,
   (d) 0.3-0.6% tert-butyl-perisononanoate,
   (e) 0.3-0.6% benzopinacol,
   (f) 0.05-0.5% 2,4-dihydroxybenzophenone, and
   (g) 35-38% fractured acrylic polymers.

* * * * *